US00PP15130P2

(12) United States Plant Patent
Post

(10) Patent No.: US PP15,130 P2
(45) Date of Patent: Aug. 31, 2004

(54) CHRYSANTHEMUM PLANT NAMED 'MANAGUA ORANGE'

(50) Latin Name: *Chrysanthemum×morifolium*
Varietal Denomination: Managua Orange

(75) Inventor: Arie Gerard Post, 's-Gravenzande (NL)

(73) Assignee: Deliflor Royalties, B.V, Maasdijk (NL)

( * ) Notice: Subject to any disclaimer, the term of this patent is extended or adjusted under 35 U.S.C. 154(b) by 0 days.

(21) Appl. No.: 10/654,565

(22) Filed: Sep. 2, 2003

(51) Int. Cl.[7] ..... A01H 5/00
(52) U.S. Cl. ..... Plt./286
(58) Field of Search ..... Plt./286

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of Chrysanthemum plant named 'Managua Orange', characterized by its daisy type inflorescences with orange-colored ray and green-colored disc florets; strong and erect flowering stems; early flowering response; good postproduction longevity; and resistance to Tomato Spotted Wilt Virus.

1 Drawing Sheet

Botanical classification/cultivar designation: *Chrysanthemum×morifolium* cultivar Managua Orange.

BACKGROUND OF THE INVENTION

The present invention relates to a new and distinct cultivar of Chrysanthemum plant, botanically known as *Chrysanthemum×morifolium* and referred to by the name 'Managua Orange'.

The new Chrysanthemum is a naturally occurring whole plant mutation of the Chrysanthemum cultivar Managua, disclosed in U.S. Plant Pat. No. 14,053. The new Chrysanthemum was discovered and selected by the Inventor on Oct. 24, 2001 within a population of plants of the cultivar Managua in a controlled environment in 's Gravenzande, The Netherlands.

Asexual reproduction of the new Chrysanthemum by terminal cuttings in 's Gravenzande, The Netherlands since Dec. 3, 2001, has shown that the unique features of this new Chrysanthemum are stable and reproduced true to type in successive generations.

BRIEF SUMMARY OF THE INVENTION

The cultivar Managua Orange has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Managua Orange'. These characteristics in combination distinguish 'Managua Orange' as a new and distinct cultivar:

1. Daisy type inflorescences with orange-colored ray and green-colored disc florets; typically grown as a spray type.
2. Strong and erect flowering stems.
3. Early flowering response.
4. Good postproduction longevity.
5. Resistant to Tomato Spotted Wilt Virus.

Plants of the new Chrysanthemum differ from plants of the parent, the cultivar Managua, primarily in ray floret coloration as plants of the cultivar Managua have orange red-colored ray florets.

Plants of the new Chrysanthemum can be compared to plants of the Chrysanthemum cultivar Tiger, disclosed in U.S. Plant Pat. No. 5,064. In side-by-side comparisons conducted in 's Gravenzande, The Netherlands, plants of the new Chrysanthemum differed from plants of the cultivar Tiger in the following characteristics:

1. Plants of the new Chrysanthemum flowered earlier than plants of the cultivar Tiger.
2. Plants of the new Chrysanthemum were more freely flowering than plants of the cultivar Tiger.
3. Plants of the new Chrysanthemum had rounded ray florets than plants of the cultivar Tiger.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Chrysanthemum.

The photograph at the top of the sheet comprises a side perspective view of a typical flowering stem of 'Managua Orange'.

The photograph at the bottom of the sheet comprises a close-up view of typical leaves and inflorescences of 'Managua Orange'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown during the spring in 's Gravenzande, The Netherlands, under commercial practice in a glass-covered greenhouse. Plants were initially given long day/short night treatments followed by short day/long night treatments to induce flower initiation and development. During the production of the plants, day temperatures were about 18° C. and night temperatures were about 17° C. Plants were about ten weeks from planting when the photographs and description were taken.

Botanical classification: *Chrysanthemum×morifolium* cultivar Managua Orange.

Commercial classification: Daisy type Chrysanthemum typically grown as a spray-type cut flower.

Parentage: Naturally occurring whole plant mutation of *Chrysanthemum×morifolium* cultivar Managua, disclosed in U.S. Plant Pat. No. 14,053.

Propagation:

*Type.*—Terminal tip cuttings.

*Time to initiate roots, summer.*—About 5 days at 20° C.

*Time to initiate roots, winter.*—About 6 days at 18° C.

*Time to produce a rooted cutting, summer.*—About 10 days at 20° C.

*Time to produce a rooted cutting, winter.*—About 14 days at 18° C.

*Root description.*—Fine and freely branching; white in color.

Plant description:

*Appearance.*—Herbaceous daisy-type cut Chrysanthemum; typically grown as a spray type; erect and strong flowering stems.

*Growth rate.*—Moderate; moderately vigorous.

*Flowering stem description.*—Length: About 80 cm. Diameter, at apex: About 6 mm. Strength: Strong. Aspect: Erect. Branching habit: Plants are typically grown as single stems. Color: 144A.

*Foliage description.*—Arrangement: Alternate. Length: About 11.5 cm. Width: About 8 to 9 cm. Apex: Mucronate. Base: Truncate to attenuate. Margin: Pinnately lobed. Texture: Rough; both surfaces pubescent. Petiole length: About 1.5 to 2 cm. Petiole diameter: About 2 to 3 mm. Color: Developing foliage, upper surface: 137A. Developing foliage, lower surface: 137C. Fully expanded foliage, upper surface: Darker than 137A. Fully expanded foliage, lower surface: 147B. Venation, upper surface: More pale than 146A. Venation, lower surface: More pale than 146B. Petiole, upper and lower surfaces: More yellow than 146B.

Inflorescence description:

*Appearance.*—Daisy type inflorescence form with elongated oblong-shaped ray florets. Inflorescences borne on terminals above foliage. Disk and ray florets develop acropetally on a capitulum. Not fragrant. Typically grown as a spray type.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 53 days later.

*Postproduction longevity.*—Inflorescences will maintain good substance and form for about 3.5 weeks after harvesting.

*Quantity of inflorescences per flowering stem.*—About 17 inflorescences per flowering stem.

*Inflorescence size.*—Diameter: About 6 cm. Depth (height): About 2 cm. Diameter of disc: About 1.6 cm.

*Inflorescence buds.*—Length: About 6 mm. Diameter: About 8 mm. Shape: Oblate. Color: 148B.

*Ray florets.*—Length, fully developed: About 2.8 cm. Width, fully developed: About 1.3 cm. Shape: Elongate oblong to somewhat spatulate. Apex: Rounded. Base: Fused; obtuse. Margin: Entire. Texture: Smooth, glabrous. Number of ray florets per inflorescence: About 20 to 24. Color: When opening, upper surface: 172C. When opening, lower surface: 163A. Fully opened, upper surface: 168B. Fully opened, lower surface: 162A.

*Disc florets.*—Shape: Tubular. Length: About 4 mm. Width: About 1 mm. Number of disc florets per inflorescence: About 180 to 210. Color: Immature: 144C. Mature: 144B.

*Peduncles.*—Length, terminal peduncle: About 4 cm. Length, fourth peduncle: About 7.5 cm. Diameter: About 2 mm. Angle: About 45° from vertical. Texture: Pubescent. Color: 138A.

*Reproductive organs.*—Androecium: Present on disc florets only. Anther color: 12A. Pollen color: 12A. Gynoecium: Present on both ray and disc florets.

*Seed/fruit.*—Seed and fruit production has not been observed.

Disease/pest resistance: Plants of the new Chrysanthemum have been observed to be resistant to Tomato Spotted Wilt Virus. Plants of the new Chrysanthemum have not been observed to be resistant to other known pathogens and pests common to Chrysanthemum.

It is claimed:

1. A new and distinct cultivar of Chrysanthemum plant named 'Managua Orange', as illustrated and described.

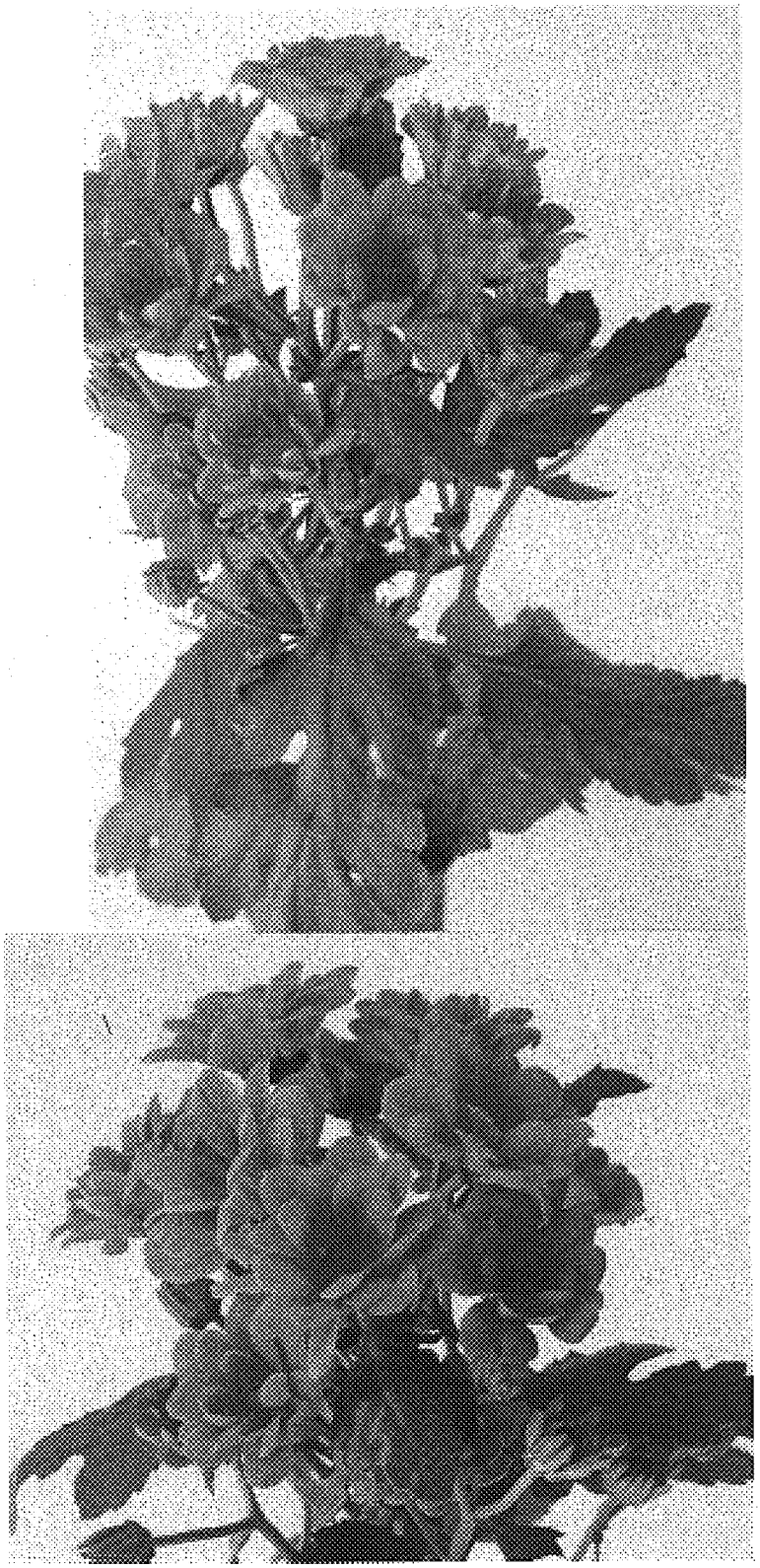

* * * * *